United States Patent

Saldivar

[11] Patent Number: 5,980,542
[45] Date of Patent: Nov. 9, 1999

[54] TONGUE CLEANER

[76] Inventor: Nilsa M. Saldivar, 7100 S. Brook Dr., Austin, Tex. 78736

[21] Appl. No.: 09/236,198

[22] Filed: Jan. 23, 1999

[51] Int. Cl.$^6$ .................................................. A61B 9/00
[52] U.S. Cl. ........................... 606/161; 606/162; 606/161
[58] Field of Search .................................. 606/160, 161, 606/162, 163; 15/23, 105, 22, 24, 322, 398; 433/91, 166

[56] References Cited

U.S. PATENT DOCUMENTS

| | | | |
|---|---|---|---|
| 1,080,929 | 12/1913 | Romeo | 606/161 |
| 1,983,601 | 11/1934 | Conn | 606/161 |
| 4,845,796 | 7/1989 | Mosley | 15/23 |

*Primary Examiner*—Michael Buiz
*Assistant Examiner*—Lien Ngo
*Attorney, Agent, or Firm*—David W. Quimby

[57] ABSTRACT

An attachment head for a prophy angle comprises a convex shape body with a plurality of radial ridges on an outside surface of the body. The attachment head rotationally cleans the upper surface of a tongue and removes foreign material and bacteria from the tongue. The attachment head can be used with or without a cleaning compound.

9 Claims, 1 Drawing Sheet

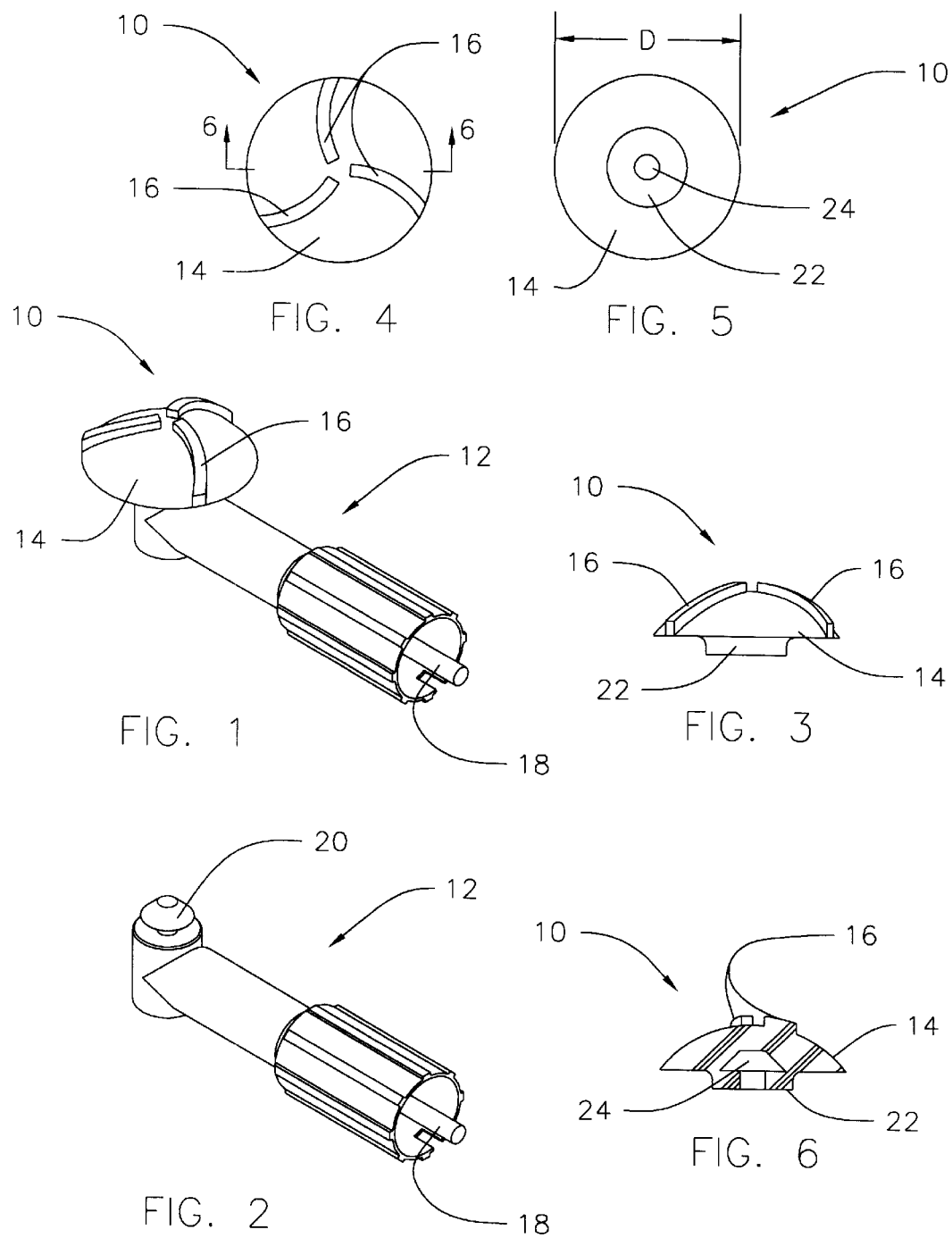

TONGUE CLEANER

BACKGROUND OF THE INVENTION

(1) Field of the invention

This invention relates to a tongue hygiene device, and more particularly to a tongue cleaner which attaches to a prophy angle. The tongue cleaner allows the tongue to be cleaned by rotary motion to minimize bacteria and foreign matter buildup on the surface of the tongue.

(2) Description of related art

Many microorganisms locate on the surface of the tongue. These microorganisms cause a variety of harmful oral diseases, plaque buildup and halitosis. It is desirable to clean the surface of the tongue; but the tongue's irregular surface, the tongue's flexibility, and the gag reflex when something is placed too far back on the tongue make cleaning the tongue difficult. The tongue's surface has microscopic projections and cavities formed by papillae and lymph follicles. The tongue also has a number of macroscopic ridges and grooves.

Several prior art methods exist for cleaning the surface of the tongue. These methods include scraping the surface of the tongue with a tongue scraper, brushing the tongue with a toothbrush or tongue brush, and blasting the surface of the tongue with an abrasive fluid.

One type of tongue scraper comprises a handle which has a cross bar with a scraping edge at an end of the handle. To clean the tongue, the user inserts the handle into the mouth so that the scraping edge contacts the back or inner end of the tongue. The user then draws the tongue scraper forward while maintaining a steady downward pressure on the tongue scraper. Foreign material stripped from the surface of the tongue collects on a surface of the tongue scraper adjacent to the scraping edge. Sometimes, large sections of the tongue surface are not cleaned because of movement of the tongue during the tongue scraping.

Brushing the tongue to remove foreign material is typically done with a toothbrush and a mild abrasive, such as toothpaste. Cleaning the tongue with a toothbrush and toothpaste is often inefficient due to the size of the toothbrush head and the softness of the bristles. The efficiency of cleaning the tongue with a brush can be improved by using a tongue brush. The design of the tongue brush head and the hardness of the bristles of a tongue brush improve the efficiency of a tongue brush for cleaning the surface of a tongue as compared to a toothbrush. Large sections of the tongue surface are not cleaned because of movement of the tongue during the tongue brushing.

Another method of cleaning the tongue is to blast the surface of the tongue with an abrasive fluid to "sandblast" the tongue. This aggressive treatment is sometimes used as a regular treatment for people suffering from severe halitosis.

When a person has a dental checkup, a dental hygienist or dentist cleans the person's teeth both under and above the gums. Then, the teeth are polished using either a prophy jet or prophy cup to complete the cleaning phase of the dental checkup. Typically, the tongue is not cleaned during a dental checkup. Cleaning the tongue during a checkup would provide the patient with a cleaner, fresher mouth. Also, cleaning the tongue would significantly reduce the presence of bacteria and foreign matter that causes plaque, gum disease and bad breath.

SUMMARY OF THE INVENTION

(1) Progressive contribution to the art

I invented a tongue cleaning head for a prophy angle which rotationally cleans the upper surface of a tongue. The prophy angle connects to a dental handpiece. When the dental handpiece is turned on, the tongue cleaner rotates. The tongue cleaner comprises a convex shaped head with a plurality of ridges located on an upper surface of the head. The size of the head of the tongue cleaner allows for easy entrance of the device into a mouth cavity. The size of the head also allows a wide area of the tongue to be cleaned. The convex shape of the tongue cleaner allows all areas of the tongue surface to be cleaned, even when the tongue moves during the cleaning process.

To clean a tongue, the user guides the rotating head of the tongue cleaner over the surface of the tongue. The tongue can be cleaned with or without the use of an abrasive paste. The ridges on the head scrape bacteria and foreign material away from the surface of the tongue. The size and shape of the head allows the entire surface of the tongue to be quickly and efficiently cleaned.

(2) Objects of this invention

An object of this invention is to provide a tongue cleaner which rotationally cleans a tongue wherein the tongue cleaner attaches to a prophy angle.

Another object is to provide a tongue cleaner with a diameter that allows for quick cleaning of the tongue, yet is sufficiently small to allow for easy entrance of the device into the mouth cavity.

Another object is to provide a tongue cleaner which rotationally cleans a tongue wherein the tongue cleaner has a convex shape and a plurality of ridges to remove foreign material and bacteria from the surface of the tongue.

Another object is to provide a dental hygienist or dentist with a device to rapidly and easily clean a tongue so that the dental hygienist or dentist can thoroughly clean a patient's mouth during the cleaning phase of a dental checkup.

Further objects are to achieve the above with a device which is sturdy, compact, durable, light-weight, simple, safe, efficient, versatile, ecologically compatible, energy conserving, reliable, and easy to manufacture.

The specific nature of the invention, as well as other objects, uses, and advantages thereof, will clearly appear from the following description and from the accompanying drawings, the different views of which are not necessarily scale drawings.

BRIEF DESCRIPTION OF THE DRAWINGS

FIG. 1 is perspective view of the tongue cleaning device of the present invention attached to a prophy angle.

FIG. 2 is a perspective view of a prophy angle.

FIG. 3 is a front elevational view of the tongue cleaning device.

FIG. 4 is a top elevational view of the tongue cleaning device.

FIG. 5 is a bottom elevational view of the tongue cleaning device.

FIG. 6 is a sectional view of the tongue cleaning device taken substantially along line 6—6 of FIG. 4.

As an aid to correlating the terms of the claims to the exemplary drawings the following catalogue of elements is provided:

10 tongue cleaner
12 prophy angle
14 body
16 ridge 18 input shaft
20 output member
22 end piece
24 recess

DESCRIPTION OF THE PREFERRED EMBODIMENTS

With reference to the drawings, FIG. 1 shows a tongue cleaner 10 attached to prophy angle 12. The tongue cleaner 10 rotationally cleans an upper surface of a tongue. The tongue cleaner 10 comprises a convex shaped body 14 which has a plurality of ridges 16 formed on an upper surface of the body. The tongue cleaner 10 and prophy angle 12 form a disposable unit which a dental hygienist or dentist uses to clean a patient's tongue.

FIG. 2 shows a prophy angle 12. Input shaft 18 of the prophy angle connects to a dental handpiece (not shown). When the dental handpiece is turned on, the dental handpiece rotates input shaft 18 of the prophy angle 12. Rotation of the input shaft 18 causes rotation of output member 20. When a tongue cleaner 10 is attached to the output member 20, as is shown in FIG. 1, rotation of the input shaft 18 causes the tongue cleaner to rotate.

FIGS. 3–5 show elevational views of tongue cleaner 10. As shown in these figures, the tongue cleaner 10 has body 14, a plurality of ridges 16 and end piece 22. A semi-rigid elastic material, such as a semi-rigid rubber, forms the tongue cleaner 10. The body 14 has a convex shaped upper surface with a plurality of ridges 16.

The tongue cleaner 10 has diameter D as shown in FIG. 5. Preferably, the diameter D is approximately 1.8 centimeters. This diameter allows the tongue cleaner 10 to be easily inserted into a mouth cavity, while still allowing a wide area of tongue to be cleaned.

The prophy angle 12 has output member 20 which snaps into recess 24 in the end piece 22 and the body 14. The recess 24 is shown in FIG. 6. In this embodiment, the tongue cleaner 10 can be easily connected to and removed from the prophy angle 12. When the dental handpiece rotates the input shaft 18 of the prophy angle 12, the output member 20 rotates the tongue cleaner 10.

Alternatively, the tongue cleaner 10 can have a permanently attached shaft member (not shown) which is the output member 20 of the prophy angle 12. In this embodiment, the tongue cleaner 10 is a part of the prophy angle 12; and the tongue cleaner 10 is not removable from the prophy angle. When the dental handpiece rotates the input shaft 18 of the prophy angle 12, the output member 20 rotates the tongue cleaner 10.

To clean a tongue, the user attaches a prophy angle 12 to a dental handpiece. A tongue cleaner 10 connects to the prophy angle 12. The user inserts the tongue cleaner 10 into a patient's mouth above the patient's tongue. The user turns on the dental handpiece to rotate the tongue cleaner 10. Then, the user contacts the tongue with the rotating tongue cleaner 10 and guides the tongue cleaner over the surface of the tongue. When the user guides the rotating tongue cleaner 10 over the surface of the tongue, the tongue cleaner can be precessed so that the tongue cleaner contacts all areas of the tongue surface, even if the tongue moves or flexes. The tongue can be cleaned with or without the use of an abrasive paste. The ridges 16 of the tongue cleaner 10 scrape bacteria and foreign material away from the surface of the tongue. The size and shape of the tongue cleaner 10 allows the entire surface of the tongue to be quickly and efficiently cleaned.

The embodiments shown and described above are only exemplary. I do not claim to have invented all the parts, elements, or steps described. Various modifications can be made in the construction, material, arrangement, and operation, and still be within the scope of my invention.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

1. A tongue cleaner for rotationally cleaning a tongue comprising:

a convex shaped body having a front surface and a back surface;

a plurality of ridges formed on the front surface of the body; and a prophy angle connected to the back surface of the body such that rotation of an input shaft of the prophy angle causes rotation of the body.

2. The tongue cleaner for rotationally cleaning a tongue as defined in claim 1 wherein said body has approximately a 1.8 centimeter diameter.

3. The tongue cleaner for rotationally cleaning a tongue as defined in claim 1 wherein said front surface of the body and said plurality of ridges are made of a semi-rigid elastic material.

4. An attachment head for a prophy angle which allows cleaning of a tongue comprising:

a body having a convex shaped surface and a back surface;

a plurality of ridges formed on the convex shaped surface of the body; and a connector between the prophy angle and the body which rotationally attaches the back surface of the body to the prophy angle.

5. The attachment head for a prophy angle as defined in claim 4 wherein a semi-rigid elastic material forms the body and the ridges.

6. The attachment head for a prophy angle as defined in claim 4 wherein wherein said body has approximately a 1.8 centimeter diameter.

7. A method of cleaning a tongue comprising:

attaching a convex shaped cleaning head to a prophy angle, said cleaning head having a plurality of ridges on an upper surface;

attaching the prophy angle to a dental handpiece;

inserting the cleaning head into a mouth cavity above an upper surface of the tongue to be cleaned;

turning on the dental handpiece to rotate the cleaning head;

contacting the surface of the tongue with the rotating cleaning head; and guiding the cleaning head over the surface of the tongue to clean the tongue.

8. The method for cleaning a tongue as defined in claim 7 further comprising applying an abrasive paste to the cleaning head before turning on the dental handpiece to rotate the cleaning head.

9. The method for cleaning a tongue as defined in claim 7 further comprising applying an abrasive paste to the surface of the tongue before contacting the surface of the tongue with the rotating cleaning head.

* * * * *